United States Patent
Nakajima et al.

(10) Patent No.: US 9,116,111 B2
(45) Date of Patent: Aug. 25, 2015

(54) ACOUSTIC SIGNAL RECEIVING APPARATUS AND IMAGING APPARATUS

(75) Inventors: Takao Nakajima, Kyoto (JP); Yasufumi Asao, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 11 days.

(21) Appl. No.: 14/123,234

(22) PCT Filed: Jul. 11, 2012

(86) PCT No.: PCT/JP2012/068261
§ 371 (c)(1),
(2), (4) Date: Dec. 2, 2013

(87) PCT Pub. No.: WO2013/012019
PCT Pub. Date: Jan. 24, 2013

(65) Prior Publication Data
US 2014/0118749 A1 May 1, 2014

(30) Foreign Application Priority Data

Jul. 19, 2011 (JP) ................................ 2011-157908

(51) Int. Cl.
*G01B 11/02* (2006.01)
*G01N 29/24* (2006.01)
(Continued)

(52) U.S. Cl.
CPC ............. *G01N 29/2418* (2013.01); *G01H 9/00* (2013.01); *G01H 9/002* (2013.01); *G01N 21/1702* (2013.01); *A61B 5/0095* (2013.01)

(58) Field of Classification Search
CPC ..... G01H 9/00; G01H 9/002; G01N 21/1702; G01N 29/2418; A61B 5/0095
See application file for complete search history.

(56) References Cited

U.S. PATENT DOCUMENTS 6,839,496 B1 * 1/2005 Mills et al. ..................... 385/126
7,095,505 B1 * 8/2006 Beard et al. ................... 356/502
(Continued)

FOREIGN PATENT DOCUMENTS

WO WO 2011/093108 A 8/2011

OTHER PUBLICATIONS

S. Ashkenazi et al., "Tissue Microscopy using Optical Generation and Detection of Ultrasound", *2005 IEEE Ultrasonics Symposium*, pp. 269-273 (Sep. 18, 2005).
(Continued)

*Primary Examiner* — Michael A Lyons
(74) *Attorney, Agent, or Firm* — Fitzpatrick, Cella, Harper & Scinto

(57) ABSTRACT

There is used an acoustic signal receiving apparatus including a wavelength-tunable light source for irradiating measurement light, a controller for controlling a wavelength of the measurement light, a Fabry-Perot probe having a first mirror on a side where the measurement light enters, a second mirror on a side where an elastic wave from an object enters, and a spacer film positioned between the first and second mirrors and deforms in response to the elastic wave, an array photosensor for detecting a reflected light amount of the measurement light by the Fabry-Perot probe, and a signal processor for acquiring an intensity of the incident elastic wave based on a change in the reflected light amount. The controller sweeps the wavelength of the measurement light, and the signal processor determines the wavelength based on the reflected light amount at each wavelength subjected to the sweep.

8 Claims, 11 Drawing Sheets

(51) Int. Cl.
  *G01H 9/00*   (2006.01)
  *G01N 21/17*  (2006.01)
  *A61B 5/00*   (2006.01)

(56) References Cited

U.S. PATENT DOCUMENTS

| | | | |
|---|---|---|---|
| 8,649,022 B2* | 2/2014 | Montgomery et al. | 356/502 |
| 2001/0046052 A1* | 11/2001 | Toida | 356/480 |
| 2011/0083509 A1 | 4/2011 | Li et al. | 600/407 |
| 2012/0157837 A1 | 6/2012 | Nagata et al. | 600/437 |
| 2013/0160557 A1 | 6/2013 | Nakajima et al. | 73/655 |

OTHER PUBLICATIONS

M. Lamont et al., "2D Imaging of ultrasound fileds using CCD array to map output of Fabry-Perot polymer film sensor", *Electronics Letters,* 42, 3 (Feb. 2, 2006).

E. Zhang et al., "Backward-mode multiwavelength photoacoustic scanner using a planar Fabry-Perot polymer film ultrasound sensor for high-resolution three-dimensional imaging of biological tissues", *Applied Optics,* 47, 561-577 (Feb. 1, 2008 issue).

\* cited by examiner

ACOUSTIC SIGNAL RECEIVING APPARATUS AND IMAGING APPARATUS

TECHNICAL FIELD

The present invention relates to an acoustic signal receiving apparatus and an imaging apparatus.

BACKGROUND ART

In general, an imaging apparatus using X-rays, ultrasound, or MRI (magnetic resonance imaging) is widely used in the fields of medical care and non-destructive inspection. On the other hand, studies on an optical imaging apparatus in which light emitted from a light source such as a laser or the like is propagated in an object such as a biological object or the like and information in the object is obtained by detecting the propagated light are actively conducted in the field of medical care. As one of the optical imaging technologies, photoacoustic tomography (PAT) is proposed.

In the technology of PAT, pulsed light generated from a light source is irradiated to an object, and an acoustic wave (hereinafter referred to as a photoacoustic wave) generated from a biological tissue that has absorbed energy of the light propagated/diffused in the object is detected at a plurality of positions. Subsequently, these signals are analyzed and information related to optical characteristic values of the internal portion of the object is visualized. With this operation, an optical characteristic value distribution in the internal portion of the object, especially a light energy absorption density distribution can be obtained.

An example of a detector for the acoustic wave includes a transducer using a piezoelectric phenomenon and a transducer using a change in capacitance and, in recent years, a detector using optical resonance is developed (Non Patent Literature 1: NPL 1). In addition, there is an example of a report on the detection of a sound pressure of ultrasound irradiated to a Fabry-Perot interferometer by using a CCD camera as a two-dimensional array sensor (Non Patent Literature 2: NPL 2).

FIG. 1 is a diagram of an acoustic wave detector using the optical resonance. As shown in the drawing, a structure in which light is resonated between reflection plates arranged in parallel with each other is called a Fabry-Perot interferometer. Hereinafter, the acoustic wave detector using the Fabry-Perot interferometer is referred to as a Fabry-Perot probe.

Such probe has a structure 103 in which a polymer film 104 having a thickness d is interposed between a first mirror 101 and a second mirror 102. Measurement light 105 is irradiated to the interferometer from the first mirror 101. At this point, a light amount Ir of reflection 106 is given by the following Expression (1):

[Math. 1]

$$I_r = \frac{4R\sin^2\frac{\varphi}{2}}{(1-R)^2 + 4R\sin^2\frac{\varphi}{2}} I_i \quad (1)$$

$$\varphi = \frac{4\pi}{\lambda_0} nd \quad (2)$$

Where $I_i$ represents an incident light amount of the measurement light 105, R represents a reflectance of each of the first and second mirrors 101 and 102, $\lambda_0$ represents a wavelength of the measurement light 104, d represents a distance between mirrors, and n represents a refractive index of the polymer film 104. $\varphi$ corresponds to a phase difference when the light travels between the two mirrors, and is given by Expression (2).

An example of a graph obtained by graphing a reflectance $I_r/I_i$ as the function of $\varphi$ is shown in FIG. 2A. A periodic reduction in the reflected light amount $I_r$ occurs, and the reflectance becomes lowest when $\varphi = 2 m\pi$ (m is a natural number) is satisfied. When an acoustic wave 107 enters the Fabry-Perot probe, the distance between mirrors d changes. With this change, $\varphi$ changes so that the reflectance $I_r/I_i$ changes. By measuring a change in the reflected light amount $I_r$ using a photodiode or the like, it is possible to detect the incident acoustic wave 107. As the change in the reflected light amount is larger, the intensity of the incident acoustic wave 107 is higher.

In order for the reflected light amount $I_r$ to sharply change when the acoustic wave 107 enters, it is necessary to increase the change rate of the reflectance $I_r/I_i$ with respect to the change in $\varphi$. In FIG. 2, the change rate thereof becomes largest at $\varphi_m$, i.e., the gradient becomes steep. Therefore, in the Fabry-Perot probe, it is preferable to perform the measurement after the phase difference is set to $\varphi_m$. By adjusting the wavelength $\lambda_0$ of the incident light, it is possible to set the phase difference to $\varphi_m$.

A graph obtained by graphing the reflectance $I_r/I_i$ as the function of $\lambda_0$ is shown in FIG. 2B. Setting the wavelength to $\lambda_m$ at which the change rate of the reflectance $I_r/I_i$ is largest corresponds to setting the phase difference to $\varphi_m$, and the sensitivity thereby becomes maximum.

In this manner, in the Fabry-Perot probe, by adjusting the measurement wavelength $\lambda_0$, it becomes possible to obtain high reception sensitivity by performing the measurement after setting the phase difference to $\varphi_m$.

In addition, in the Fabry-Perot probe, since the change in the reflected light amount only at a position to which the measurement light 105 is applied is measured, the spot region of the incident measurement light 105 becomes a region having the reception sensitivity. Consequently, by performing raster scanning with the measurement light using a galvanometer or the like, it is possible to obtain two-dimensional distribution data on the acoustic wave. By performing signal processing by using the obtained two-dimensional distribution data on the acoustic wave, an image is obtained.

On the other hand, by narrowing down the measurement light 105 using a lens or the like, it is possible to reduce the reception area. With this operation, the reception spot is reduced so that the resolution of the image at the time of reconstruction is improved. In addition, according to NPL 2, the Fabry-Perot probe has a wide reception frequency band of the acoustic wave. Because of the reasons described above, it becomes possible to obtain a minute image with high resolution by using the Fabry-Perot probe.

CITATION LIST

Non-Patent Literature

NPL 1: E. Zang, J. Laufer, and P. Beard, "Backward-Mode Multiwavelength Photoacoustic Scanner Using a Planar Fabry-Perot Polymer Film Ultrasound Sensor for High-Resolution Three-Dimensional Imaging of Biological Tissues", Applied Optics, 47, 561-577(2008)

NPL 2: M. Lamont, P. Beard, "2D Imaging of Ultrasound Fields Using CCD Array to Map Output of Fabry-Perot Polymer Film Sensor", Electronics Letters, 42, 3, (2006).

SUMMARY OF INVENTION

Technical Problem

However, as the result of elaborate studies by the present inventors, it is difficult to form the polymer film 104 between mirrors into the completely same thickness, and variations in in-plane film thickness occur. It has been revealed that, due to the variations, the distance between mirrors of the Fabry-Perot probe varies and variations in reception sensitivity occur depending on the position of reception of the acoustic wave.

Consequently, in NPL 1, when the two-dimensional distribution data on the acoustic wave is acquired, the wavelength of the measurement light is swept and the optimum wavelength is determined one by one while raster scanning is performed by using the galvanometer, and the measurement of the acoustic wave at the optimum wavelength is performed. However, the method has the problem that an extremely long measurement time is required.

To cope with the problem, in NPL 2 described above, a method is reported in which, instead of performing the scanning one by one, the acoustic wave distribution is obtained by irradiating incident light having a large beam diameter to the Fabry-Perot interferometer and measuring the two-dimensional distribution of the reflected light by using a two-dimensional array photosensor. That is, the incident light of a given wavelength $\lambda_1$ having the large beam diameter is irradiated to the Fabry-Perot interferometer and the two-dimensional distribution of the reflected light is measured by using the two-dimensional array photosensor, and hence, theoretically, it becomes possible to obtain data at an extremely high speed.

However, although the reception sensitivity is high in the region where the wavelength $\lambda_1$ is the optimum wavelength with respect to the film thickness, since it is extremely difficult to completely suppress variations in film thickness by present film formation technologies, a region where the sensitivity is low or a region where there is no sensitivity is generated. This leads to the problem that the production yield of a device is reduced or image quality is significantly degraded.

The present invention has been achieved in view of the above-described problem, and an object thereof is to provide a technology for measuring the two-dimensional distribution of a change in the reflected light amount of the measurement light at the optimum wavelength by the Fabry-Perot probe using the array photosensor.

Solution to Problem

The present invention provides an acoustic signal receiving apparatus comprising:
a wavelength-tunable light source for irradiating measurement light;
a controller for controlling a wavelength of the measurement light;
a Fabry-Perot probe including a first mirror positioned on a side where the measurement light enters, a second mirror positioned on a side where an elastic wave from an object enters, and a spacer film that is positioned between the first and second mirrors and deforms in response to the entrance of the elastic wave;
an array photosensor for detecting a reflected light amount of the measurement light by the Fabry-Perot probe; and
a signal processor for acquiring an intensity of the elastic wave having entered the Fabry-Perot probe based on a change in the reflected light amount resulting from the deformation of the spacer film, wherein
the controller sweeps the wavelength of the measurement light, and
the signal processor determines, based on the reflected light amount at each position of the Fabry-Perot probe that is acquired at each wavelength subjected to the sweep, the wavelength of the measurement light used at the position.

Advantageous Effects of Invention

According to the present invention, it is possible to provide a technology for measuring the two-dimensional distribution of a change in the reflected light amount of the measurement light at the optimum wavelength by the Fabry-Perot probe using the array photosensor.

Further features of the present invention will become apparent from the following description of exemplary embodiments with reference to the attached drawings.

DESCRIPTION OF EMBODIMENTS

Next, a description is given of embodiments of the present invention with reference to the drawings.

First Embodiment

Figure 3:
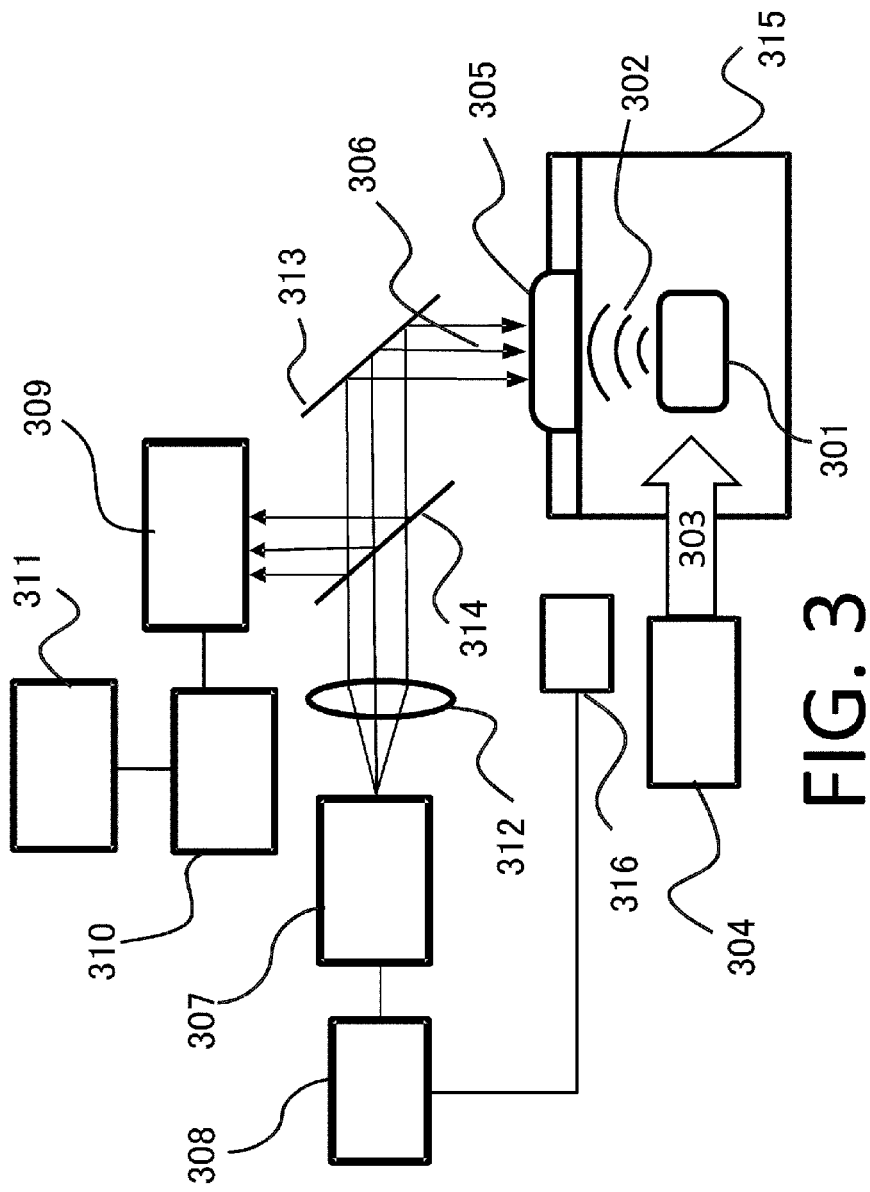
FIG. 3 is a view showing an example of a configuration of a biological object information imaging apparatus.

FIG. 3 is a view explaining an example of a configuration of an imaging apparatus in the present embodiment. The imaging apparatus is configured by providing an element for performing imaging processing based on a received acoustic wave in an acoustic signal receiving apparatus that receives the acoustic wave released from an object.

The acoustic signal receiving apparatus of the present embodiment includes an excitation light source 304 (e.g., a pulsed light source) for emitting excitation light 303 that is irradiated to an object 301 to excite a photoacoustic wave 302. When the object 301 is a biological object, it is possible to image a light absorber in the internal portion of the object 301 such as a tumor or a blood vessel in the biological object. Alternatively, it is possible to image the light absorber on the surface of the object 301. The light absorber in the internal portion or on the surface of the object 301 absorbs a part of light energy, and the photoacoustic wave 302 is thereby generated. The imaging apparatus includes a Fabry-Perot probe 305 for detecting the photoacoustic wave 302.

The Fabry-Perot probe 305 is capable of detecting a sound pressure by the irradiation of measurement light 306. The imaging apparatus includes a measurement light wavelength-tunable light source 307 for generating the measurement light 306. In addition, the imaging apparatus also includes a controller 308 for controlling the wavelength of the measurement light 306 emitted from the measurement light wavelength-tunable light source, and a photodiode (PD) 316 used for the controlling by the controller. Further, the imaging apparatus includes an array photosensor 309 for measuring a reflected light amount of the measurement light 306 having entered the Fabry-Perot probe 305 and converting the reflected light amount into an electric signal. The acoustic signal receiving apparatus is configured by the elements described above.

The imaging apparatus is configured by further providing a signal processor 310 and an image display 311 in the above-described acoustic signal receiving apparatus. That is, the imaging apparatus of the present embodiment includes the image display 311 for displaying optical characteristic value distribution information obtained by analyzing the electric signal obtained by the array photosensor 309 in the signal processor 310. When the object is a biological object, the imaging apparatus of the present embodiment can be called a biological object information imaging apparatus.

Figure 4:
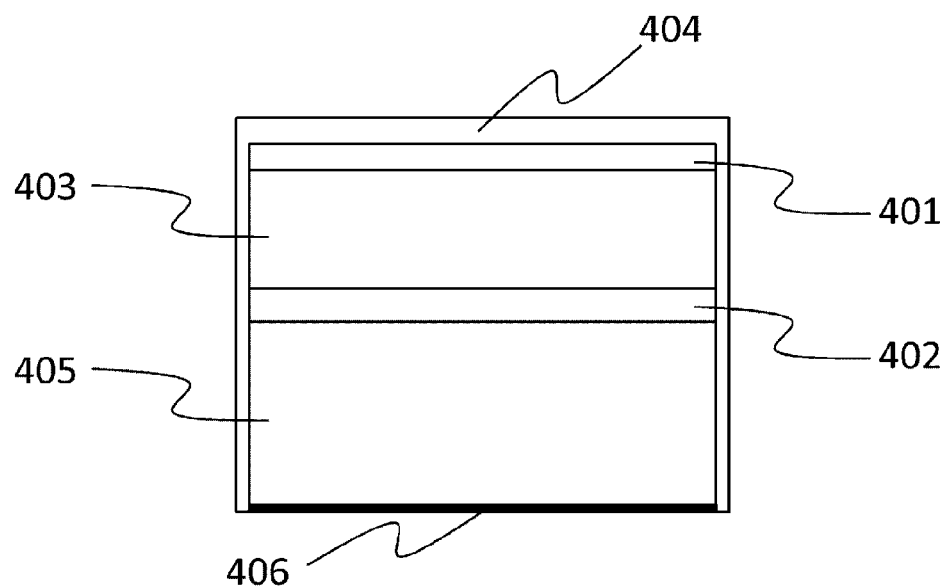
FIG. 4 is a view showing an example of a structure of a Fabry-Perot probe.

FIG. 4 is a view explaining the cross-sectional structure of the Fabry-Perot probe in the present embodiment. A first mirror 402 is a mirror positioned on the side where the measurement light enters, while a second mirror 401 opposing the first mirror 402 is a mirror positioned on the side where an elastic wave from the object enters. As the material of the first and second mirrors 402 and 401, a dielectric multilayer film or a metal film can be used. There is a spacer film 403 between the mirrors. As the spacer film 403, a film having a large strain occurring when the elastic wave enters the Fabry-Perot probe is preferable and, for example, an organic polymer film is used. In the organic polymer film, parylene, SU8, or polyethylene can be used. Any film that deforms when the acoustic wave is received can be adopted so that an inorganic film may also be used.

The entire Fabry-Perot probe is protected by a protective film 404. As the protective film 404, a film obtained by forming an organic polymer film made of parylene or the like or an inorganic film made of $SiO_2$ or the like into a thin film is used. For a substrate 405 on which the first mirror 402 is formed, glass or acrylic can be used. In order to reduce an influence resulting from the interference of light in the substrate 405, the substrate 405 is preferably in a wedge-like shape. In addition, in order to avert the reflection of light on the surface of the substrate 405, the substrate 405 is preferably subjected to an AR coating process 406.

Returning to FIG. 3, the description of the constituent element of the apparatus is continued. In addition, how to perform the measurement is described with reference to a flowchart of FIG. 6 on an as needed basis.

As the measurement light wavelength-tunable light source 307 that emits the measurement light 306 for measuring the reflected light amount of the Fabry-Perot probe 305, a wavelength-tunable laser can be used. The reflectance of the measurement light 306 to each of the first mirror 402 and the second mirror 401 is preferably 90% or more. In addition, the sweep speed when the wavelength is changed is preferably about 100 nm/s.

The measurement light 306 is magnified by a lens 312, reflected in the Fabry-Perot probe 305, and enters the array photosensor 309. With this, it is possible to obtain a reflection intensity distribution on the Fabry-Perot probe 305. As an optical system, a mirror 313 and a half mirror 314 are used. The optical system may appropriately have a configuration capable of measuring the reflectance in the Fabry-Perot probe 305, and can adopt a configuration in which a polarizing mirror and a wavelength plate are used instead of the half mirror 314, and a configuration in which an optical fiber is used. By the optical system, the position on the Fabry-Perot probe 305 is associated with a pixel on the array photosensor 309.

As the array photosensor 309, a two-dimensional array photosensor or a one-dimensional array photosensor is used. For example, a CCD sensor and a CMOS sensor can be used. However, an array photosensor other than those mentioned above can also be used as long as the array photosensor is capable of measuring the reflected light amount of the measurement light 306 when the photoacoustic wave 302 enters the Fabry-Perot probe 305 and converting the reflected light amount into the electric signal.

Figure 1:
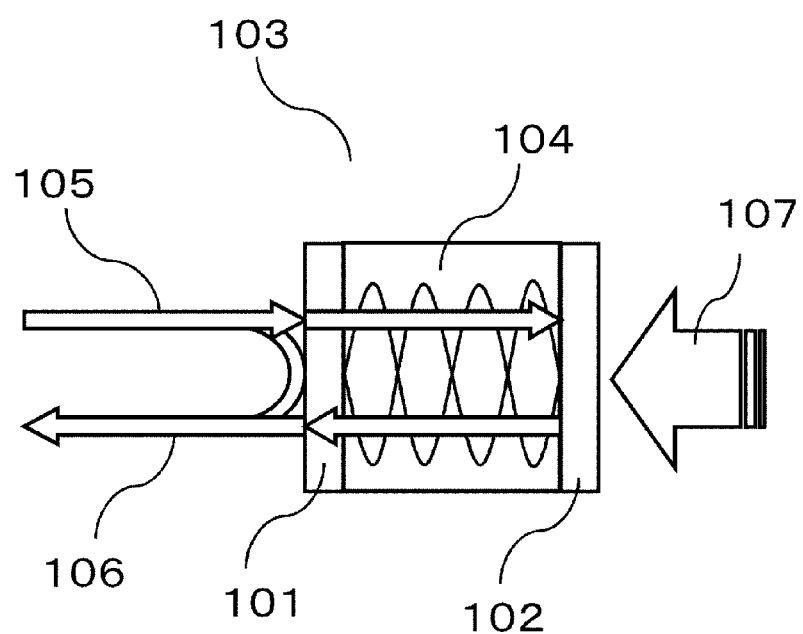
FIG. 1 is a view showing an example of a configuration of a Fabry-Perot interferometer.
Figure 2A:
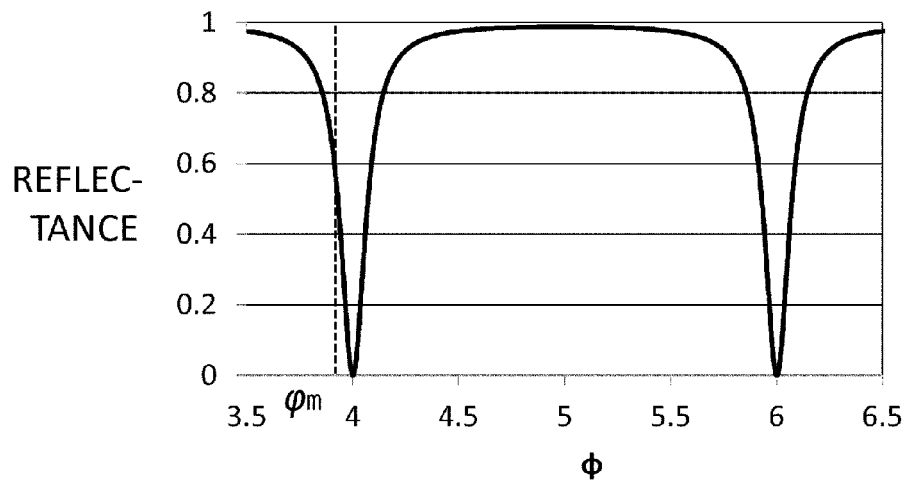
FIGS. 2A and 2B are graphs showing change in the reflectance of the Fabry-Perot interferometer.
Figure 2B:
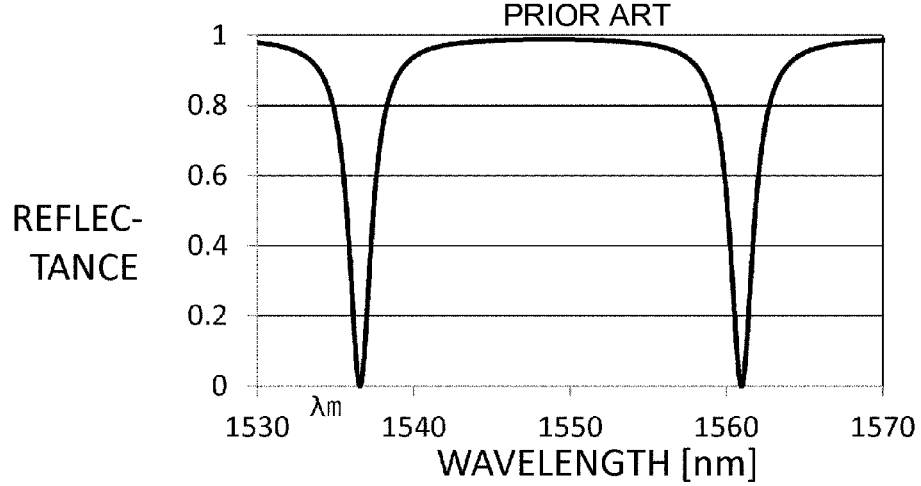

Since the distance between mirrors of the Fabry-Perot probe 305 varies depending on the position, it is necessary to determine the optimum wavelength at each position (each of associated pixels on the array photosensor 309). Accordingly, the wavelength of the measurement light 306 is swept in a specific wavelength range, the wavelength dependence of the reflected light amount as shown in FIG. 2B is measured at each pixel on the array photosensor 309, and the optimum wavelength $\lambda_m$ at which the change rate is large is determined. This processing corresponds to pre-processing in the flow of FIG. 6.

Figure 6:
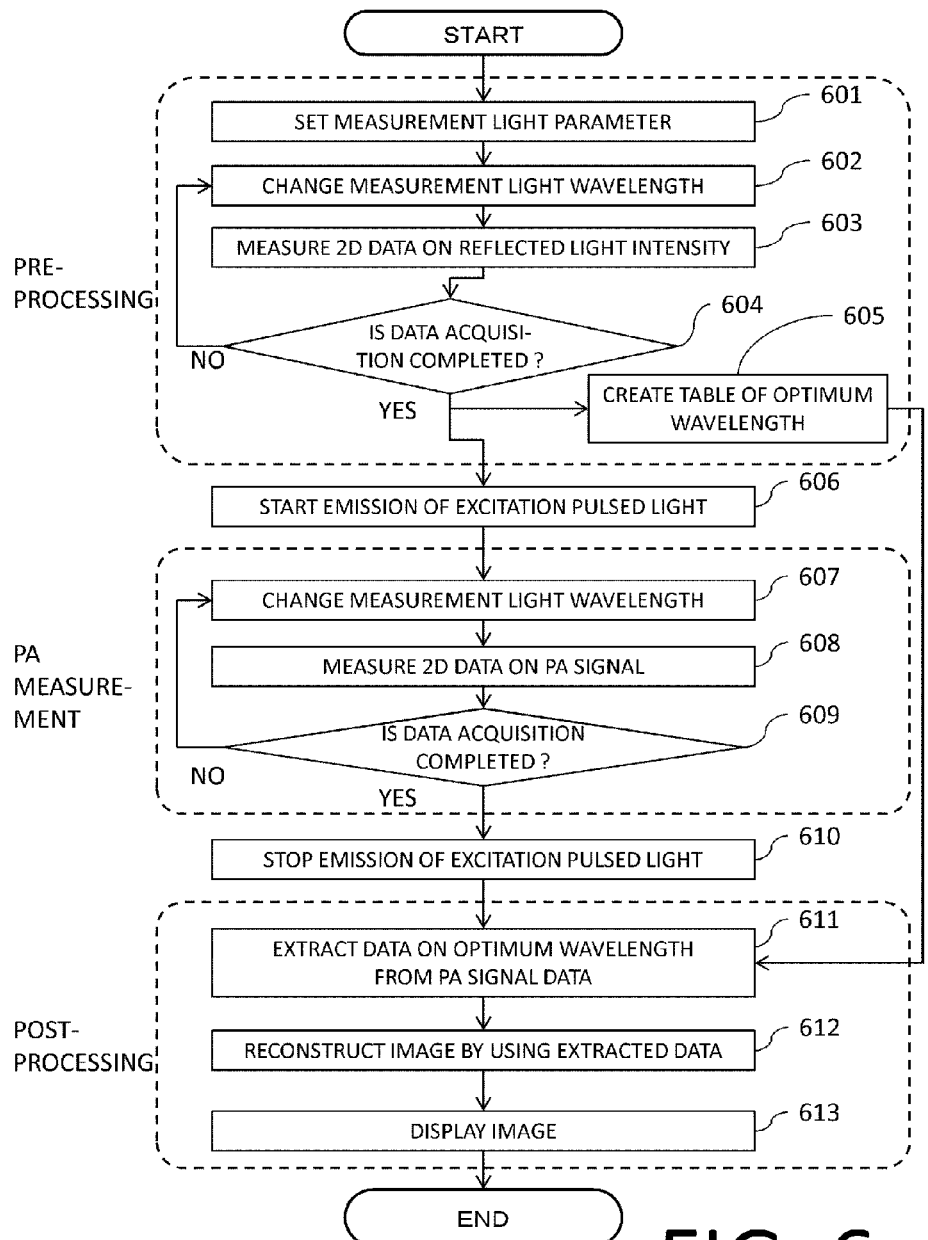
FIG. 6 is a flowchart showing an example of the processing performed by the biological object information imaging apparatus.

First, parameters of the measurement light 306 including a wavelength sweep range and a sweep step are set (Step 601 of FIG. 6). The controller 308 sweeps the wavelength of the measurement light 306 based on the specified wavelength sweep range and sweep step (Step S602). That is, the wavelength of the measurement light is changed. Since the optimum wavelength varies depending on the degree of variations in the distance between mirrors, the wavelength range to be swept is preferably set to a specific range equal to or exceeding a free spectral range. The wavelength interval for capturing data when the wavelength dependence of the reflected light amount as shown in FIG. 2 is measured is preferably minimized, and can be set to, e.g., 0.1 nm.

By determining the reflected light amount of the measurement light by using the array photosensor, the measurement of 2D data on a reflected light intensity is performed (Step S603). This measurement is continued until the end of acquisition of sweep range data in the set parameters (Step S604).

With this, the wavelength dependence of the reflected light amount at each pixel is obtained. Subsequently, by determining the wavelength $\lambda_m$ at which the reflected light amount Ir sharply changes, a table of the optimum wavelength $\lambda_m$ at each pixel is created (Step S605).

As the excitation light 303 irradiated to the object 301, light of a wavelength that allows absorption of the light in a specific component among components constituting the object 301 is used. As the excitation light 303, pulsed light can be used. The pulsed light is of the order of several picoseconds to several hundred nanoseconds and, when the object is a biological object, it is preferable to adopt the pulsed light of several nanoseconds to several tens of nanoseconds. As the light source 304 that generates the excitation light 303, a laser is preferable. However, instead of the laser, a light-emitting diode or a flash lamp can also be used.

As the laser, various lasers such as a solid laser, a gas laser, a dye laser, and a semiconductor laser can be used. When a dye or an OPO (Optical Parametric Oscillators) in which an oscillation wavelength can be converted is used, it becomes possible to measure a difference resulting from the wavelength of an optical characteristic value distribution.

As for the wavelength of the light source to be used, the range of 700 nm to 1100 nm in which absorption in the biological object is less likely to occur is preferable. However, the wavelength range wider than the above-mentioned wavelength range, e.g., the wavelength range of 400 nm to 1600 nm and, further, ranges of a terahertz wave, a microwave, and a radio wave can also be used.

In FIG. 3, the excitation wave 303 is irradiated to the object from such a direction that the excitation light 303 is not shaded by the Fabry-Perot probe 305. However, by using the wavelength that allows the excitation light 303 to pass through the mirror of the Fabry-Perot probe 305, it is also possible to irradiate the excitation light 303 from the side of the Fabry-Perot probe 305.

In order to efficiently detect the photoacoustic wave 302 generated from the object 301 using the Fabry-Perot probe 305, it is desirable to use an acoustic coupling medium between the object 301 and the Fabry-Perot probe 305. FIG. 3 is the drawing in which water is used as the acoustic coupling medium and the object 301 is disposed in a water bath 315. However, the acoustic coupling medium may appropriately be interposed between the object 301 and the Fabry-Perot probe 305. For example, a configuration may also be adopted in which a matching gel is applied to be interposed between the object 301 and the Fabry-Perot probe 305.

The excitation light 303 such as the pulsed light or the like is irradiated from the excitation light source 304 to the object 301 (Step S606 of FIG. 6). At this point, the Fabry-Perot probe 305 absorbs a part of energy of the excitation wave 303 to thereby detect the photoacoustic wave (which is an elastic wave and typically ultrasound) 302 generated from the internal portion of the object in the form of the change in the reflected light amount of the measurement light 306. The detected reflected light amount is converted into the electric signal in the array photosensor 309. The distribution of the electric signal in the array photosensor 309 represents the intensity distribution of the photoacoustic wave 302 reaching on the Fabry-Perot probe 305. With this, it is possible to obtain the pressure distribution of the photoacoustic wave 302 reaching on the Fabry-Perot probe 305.

In order to detect the photoacoustic wave 302 using the Fabry-Perot probe 305, it is necessary to measure the change in the reflected light amount of the measurement light 306 at the optimum wavelength $\lambda_m$ or the wavelength in the vicinity thereof. Consequently, a program that sweeps the wavelength of the measurement light 306 for detecting the photoacoustic wave 302 while sweeping the wavelength of the measurement light 306 is set in the controller 308. The sweep program to be set includes parameters such as the wavelength sweep range, the sweep step, a sweep speed, and a sweep time. As the sweep range and the sweep step of the wavelength of the measurement light 306, values specified when the above-described table of the optimum wavelength is created are used. The controller 308 sweeps the wavelength of the measurement light according to the specified program. With this, the measurement is performed while the wavelength of the measurement light is changed (Steps S607 to S608 of FIG. 6).

Figure 5:
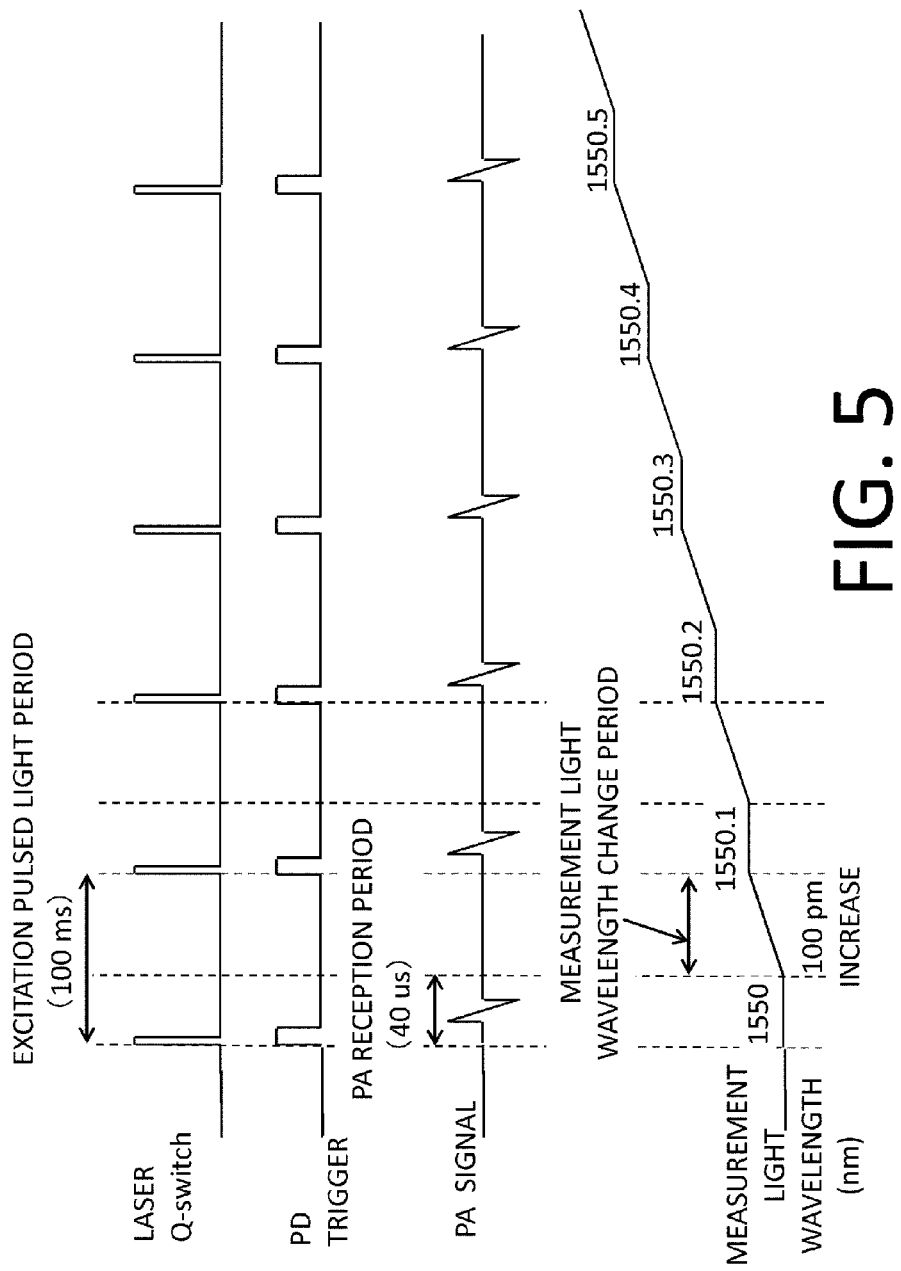
FIG. 5 is a time chart showing an example of processing performed by the biological object information imaging apparatus.

FIG. 5 shows an example of a time chart of the irradiation of the excitation light 303, the wavelength sweep of the measurement light 306, and the measurement of the photoacoustic wave. FIG. 5 shows a case where the pulse rate of the pulsed light as the excitation light 303 is 10 Hz.

In FIG. 5, the wavelength of the measurement light 306 is set to the initial wavelength by the controller 308, and the pulsed light is irradiated. In the case of a pulsed laser apparatus, this operation is performed by a Q-switch operation (uppermost portion of FIG. 5). Upon the operation, a part of the excitation light 303 is detected by the photodiode 316 and, by using this as a trigger, the photoacoustic wave 302 is measured (second and third portions from above of FIG. 5). The measurement is performed during a specific PA reception period. The reception period should be determined in accordance with the size of the object, the distance between the light absorber and the probe, and the photoacoustic wave transmission speed in the object.

Thereafter, before the next excitation light 303 is emitted, the wavelength of the measurement light 306 is increased by an input value (100 pm in this case). After the wavelength is increased, the photoacoustic wave 302 is measured at the next trigger. This operation is repeated until the sweep of the specified wavelength range is ended (lowermost portion of FIG. 5). With this, in the sweep range of the wavelength of the measurement light 306, at every wavelength at the intervals of 100 pm, the change in reflected light amount at every pixel when the photoacoustic wave 302 reaches the Fabry-Perot probe 305 is measured.

The processing described above corresponds to PA measurement (PhotoAcoustic measurement) of the flowchart of FIG. 6, and Steps S607 to S609 are repeated. When the PA measurement is finished, the emission of the excitation pulsed light is stopped (Step S610).

Note that FIG. 5 is the time chart in a case where the number of times of data acquisition is one. When the number of times of data acquisition or the pulse rate of the laser is different, it is necessary to change the time program of the controller 308 correspondingly.

After the end of the measurement of the photoacoustic wave, the step of post-processing is started.

The signal processor extracts the electric signal when the photoacoustic wave at the optimum wavelength enters at each pixel based on the table of the premeasured optimum wavelength for each pixel (Step S611 of FIG. 6).

In addition, the signal processor 310 calculates the optical characteristic value distribution of the internal portion of the object 301 based on the distribution of the extracted electric signal at the optimum wavelength $\lambda_m$ for each pixel in the array photosensor 309 (Step S612). This processing corresponds to image reconstruction, and examples of the optical characteristic value distribution include the position and the size of the light absorber, a light absorption coefficient, and a light energy accumulation amount distribution.

As a reconstruction algorithm for obtaining the optical characteristic value distribution from the obtained electric signal distribution, universal back projection, phasing addition, and the like can be adopted. The reconstructed image is displayed in the image display 311 in a specific format (Step S613). Note that a region having a significant abnormality in film thickness due to presence of a foreign object in a device can also be imaged, after considering that the region cannot be used as data, by correcting a data missing portion at the time of the image reconstruction processing.

Note that, as the signal processor 310, any processor may be used as long as the processor is capable of storing the distribution of the time-varying change in the electric signal indicative of the intensity of the photoacoustic wave 302 and converting the distribution thereof into data on the optical characteristic value distribution using operation means.

Note that, when lights of a plurality of wavelengths are used as the excitation light 303, the optical coefficient in the biological object is calculated for each wavelength and the value is compared with the wavelength dependence specific to a substance (glucose, collagen, oxygenated/reduced hemoglobin, or the like) constituting the biological tissue. With this, it is also possible to image the distribution of concentration of the substance constituting the biological object.

In the embodiment of the present invention, it is desirable to have the image display 311 for displaying image information obtained by the signal processing.

In the measurement flowchart of the present embodiment shown in FIG. 6, although the creation of the table of the optimum wavelength is performed as the pre-processing before the photoacoustic measurement (the PA measurement), the creation of the table of the optimum wavelength may also be performed after the photoacoustic measurement.

By using the biological object information imaging apparatus described in the first embodiment, it becomes possible to obtain a high-resolution photoacoustic image within a short time period by using the Fabry-Perot probe 305.

Second Embodiment

Figure 7:
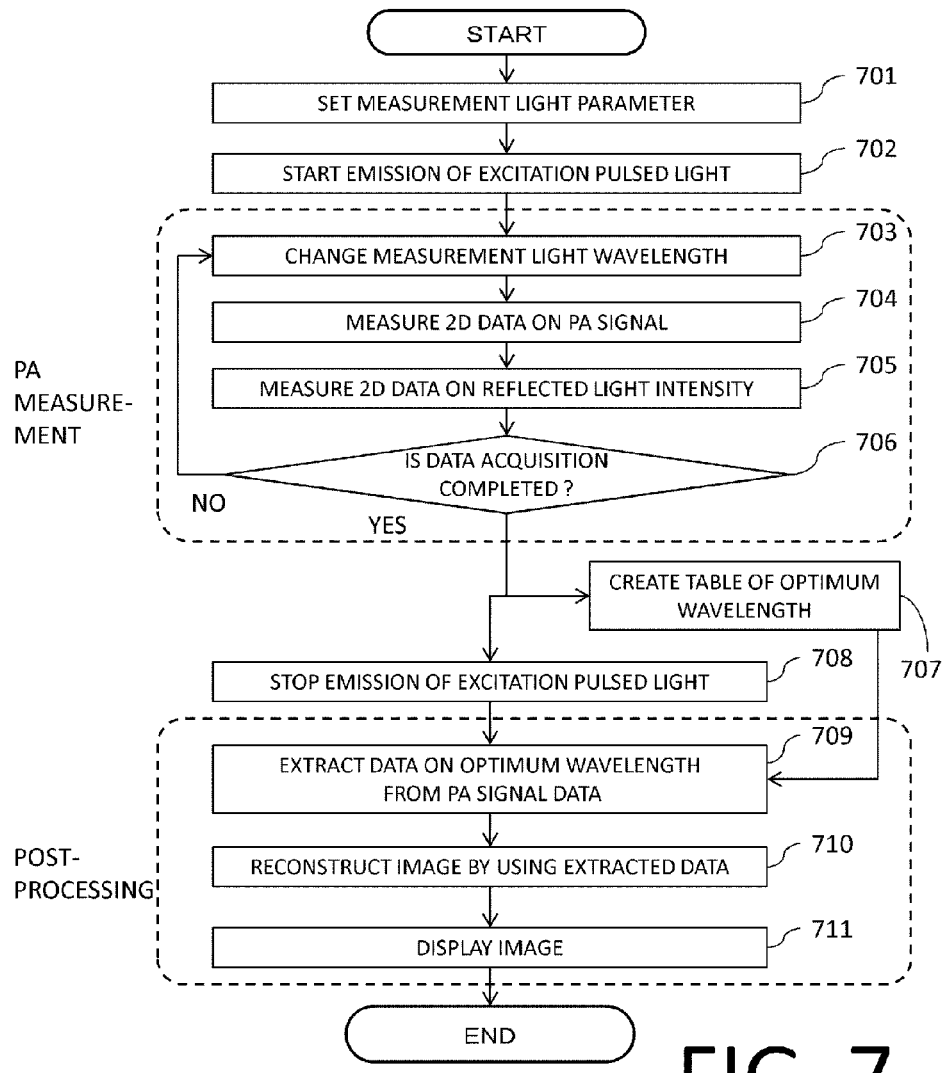
FIG. 7 is a flowchart showing an example of processing performed by the biological object information imaging apparatus.

FIG. 7 shows a measurement flowchart of a biological object information imaging apparatus of the present embodiment. In the biological object information imaging apparatus in the present embodiment, the apparatus configuration and the like other than the measurement flowchart are the same as those in the first embodiment, and hence the description thereof is omitted. In the following description, the flowchart of FIG. 7 is referenced on an as needed basis.

In the present embodiment, the measurement of the photoacoustic signal and the measurement for the creation of the optimum wavelength are not independent of each other, but they are simultaneously performed.

First, a program that sweeps the wavelength of the measurement light 306 for detecting the reflected light amount and the photoacoustic wave 302 while sweeping the wavelength of the measurement light 306 is set in the controller 308 (Step S701). The sweep program to be set includes parameters such as the wavelength sweep range, the sweep step, the sweep speed, and the sweep time.

Since the optimum wavelength varies depending on the degree of variations in the distance between mirrors, the wavelength range to be swept is preferably a wavelength range equal to or exceeding the free spectral range. The wavelength interval for capturing data when the wavelength dependence of the reflected light amount as shown in FIG. 2 is measured is preferably minimized, and can be set to, e.g., 0.1 nm.

After the program that sweeps the wavelength of the measurement light is set in the controller 308, the emission of the excitation light 303 (e.g., the pulsed light) that enters the object 301 is started (Step S702).

The wavelength of the measurement light 306 is set to the initial wavelength by the controller 308, and the change in reflected light amount caused by the photoacoustic wave from the object is measured (Step S703). That is, the data measurement of the photoacoustic signal (PA signal) (2D data measurement in the case of the array photosensor) is performed (Step S704).

Thereafter, the reflected light amount in a state where the photoacoustic wave 302 does not enter is measured. In the case of the array photosensor, the 2D data measurement of the reflected light intensity is performed (Step S705).

Subsequently, after the wavelength of the measurement light 306 is swept, when the data acquisition in the sweep range is not completed (S706=NO), the wavelength of the measurement light is changed and the change in reflected light amount caused by the photoacoustic wave 302 is measured again. The PA measurement processing from S703 to S706 is performed until the set sweep range is completed.

Figure 8:
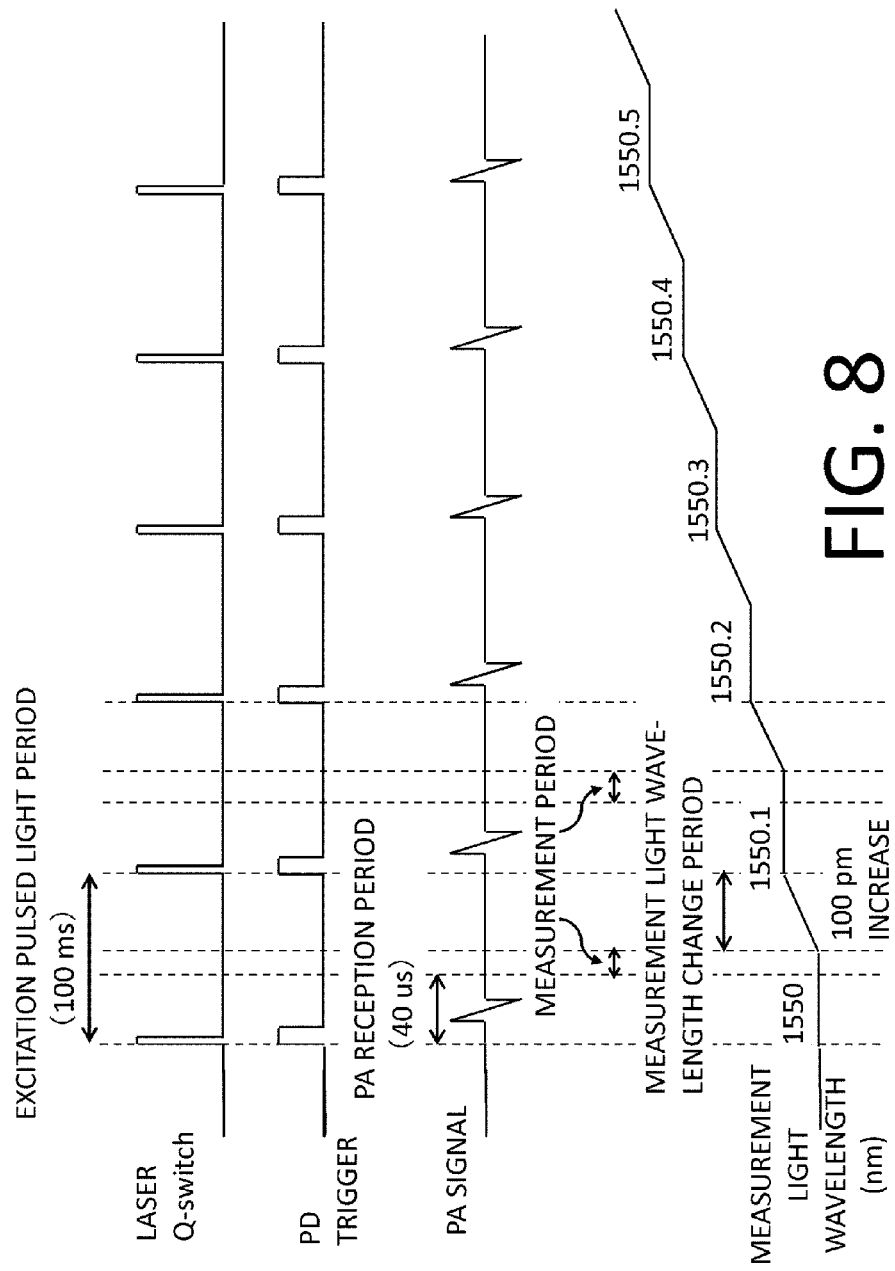
FIG. 8 is a time chart showing an example of the processing performed by the biological object information imaging apparatus.

FIG. 8 shows an example of a time chart of the irradiation of the excitation light 303, the wavelength sweep of the measurement light 306, the measurement of the photoacoustic wave, and the measurement of the reflected light amount in the state where the acoustic wave dose not enter. FIG. 8 shows a case where the pulse rate of the pulsed light as the excitation light 303 is 10 Hz.

In FIG. 8, the excitation light 303 is irradiated by the Q-switch operation (uppermost portion of FIG. 8). Then, a part of the excitation light 303 is detected by the photodiode, and the photoacoustic wave 302 is measured by using the detection as the trigger (second and third portions from above of FIG. 8). Thereafter, the reflected light amount in the state where the photoacoustic wave 302 does not enter is measured (measurement period). Further, before the next excitation light 303 is emitted, the wavelength of the measurement light 306 is increased by the input value (100 pm in this case). After the wavelength thereof is increased, at the next trigger, the photoacoustic wave 302 is measured. This operation is repeated until the sweep of the specified sweep range is ended (lowermost portion of FIG. 8). When the data acquisition is finished, the emission of the excitation light is stopped (Step S708).

Note that FIG. 8 is a time chart in the case where the number of times of data acquisition is one. When the number of times of data acquisition or the pulse rate of the excitation light source 304 is different, it is necessary to change the time program of the controller 308 correspondingly.

With this, in the swept wavelength range of the measurement light 306, the wavelength dependence of the reflected light amount in the state where the photoacoustic wave 302 does not enter at each pixel is obtained together with the photoacoustic signal 302. Subsequently, similarly to the first embodiment, by determining the wavelength $\lambda_m$ at which the reflected light amount Ir sharply changes, the table of the optimum wavelength $\lambda_m$ at each pixel is created (Step S707 of FIG. 7).

Then, the step of post-processing is started. The processing of Steps S709 to S711 is performed in the same manner as in Steps S611 to S613 of FIG. 6.

That is, the signal processor 310 extracts the electric signal when the photoacoustic wave 302 at the optimum wavelength enters at each pixel based on the created table of the optimum wavelength for each pixel after the end of the measurement of the photoacoustic wave 302. In addition, based on the distribution of the extracted electric signal at the optimum wavelength for each pixel in the array photosensor 309, the signal processor 310 calculates the optical characteristic value distribution in the internal portion of the object 301. Examples of the optical characteristic value distribution include the position and the size of the light absorber, the light absorption coefficient, and the light energy accumulation amount distribution. Subsequently, the reconstructed image is displayed in the image display 311.

By using the biological object information imaging apparatus described in the second embodiment, it becomes possible to obtain the high-resolution photoacoustic image within a short time period by using the Fabry-Perot probe.

Third Embodiment

Figure 9:
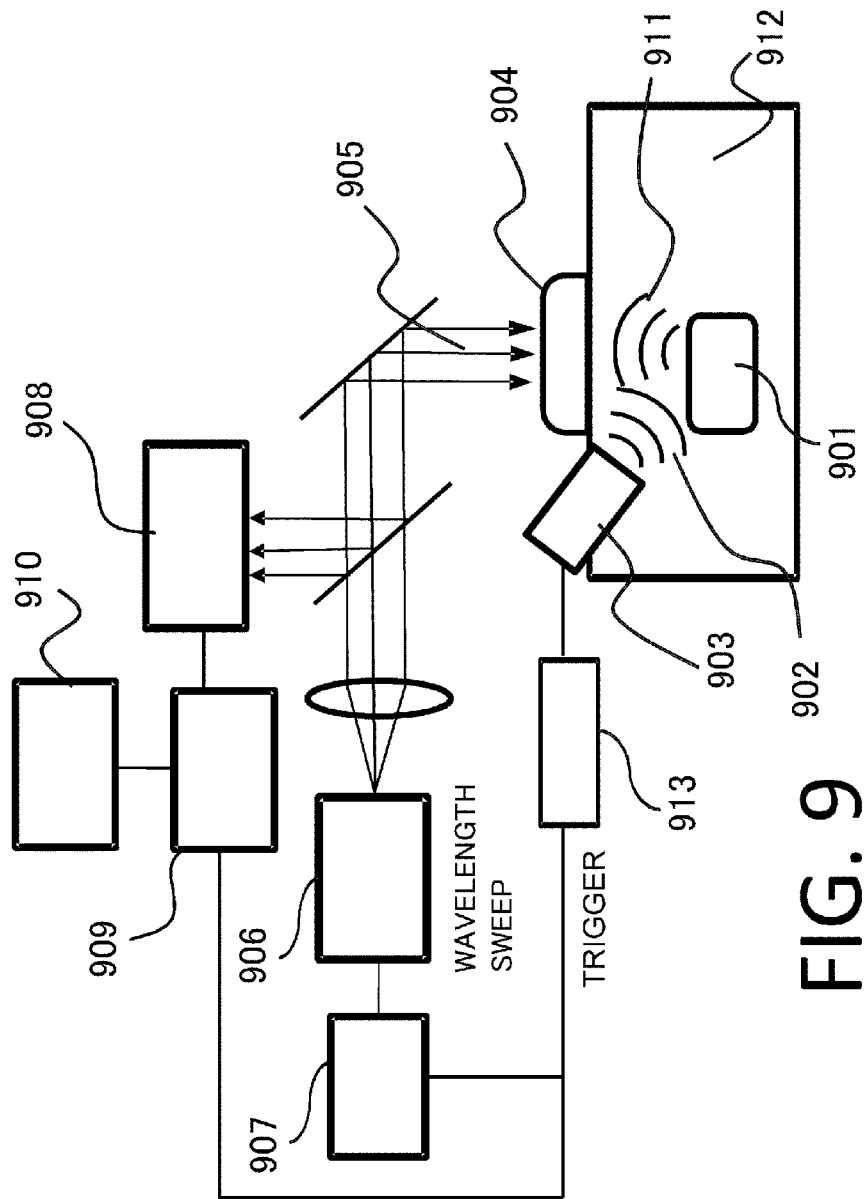
FIG. 9 is a view showing an example of a configuration of a biological object information imaging apparatus.

FIG. 9 is a view explaining an example of the configuration of a biological object information imaging apparatus in the present embodiment.

The biological object information imaging apparatus of the present embodiment allows imaging of an acoustic impedance distribution of the internal portion of the biological object based on the echo of the elastic wave (ultrasound). The description of the same configuration as that in the first embodiment is omitted.

The biological object information imaging apparatus of the present embodiment particularly includes a transducer 903 for irradiating an elastic wave 902 to an object 901, and a pulser 913 connected to the transducer.

In addition, the biological object information imaging apparatus also includes a Fabry-Perot probe 904 for detecting the elastic wave reflected at the interface of a tissue having a different acoustic impedance such as a tumor or the like in the internal portion of the object 901. Further, the biological object information imaging apparatus includes a measurement light wavelength-tunable light source 906 for emitting measurement light 905 that enters the Fabry-Perot probe 904. Furthermore, the biological object information imaging apparatus includes a controller 907 for controlling the wavelength of measurement light 905 emitted from the measurement light wavelength-tunable light source 906. In addition, the biological object information imaging apparatus includes an array photosensor 908 for measuring the reflected light amount of the measurement light 905 having entered the Fabry-Perot probe 904 and converting the measured reflected light amount into the electric signal. Though not numbered in the drawing, the measurement light is guided to a desired path by optical systems such as a lens, a mirror, and a half mirror. Further, the biological object information imaging apparatus includes a signal processor 909 for analyzing the electric signal obtained by the array photosensor 908. Furthermore, the biological object information imaging apparatus includes an image display 910 for displaying the processing result.

The configuration thereof is the same as that in the above-described embodiments. Note that what is obtained by the analysis of the signal processor 909 is acoustic impedance distribution information on the object.

Since the distance between mirrors of the Fabry-Perot probe 904 varies depending on the position, it is necessary to determine the optimum wavelength at each position. The wavelength of the measurement light 905 is swept in a given wavelength range, the wavelength dependence of the reflected light amount as shown in FIG. 2 is measured at each pixel on the array photosensor 908, and the optimum wavelength $\lambda_m$ at which the change rate is large is determined.

Figure 11:
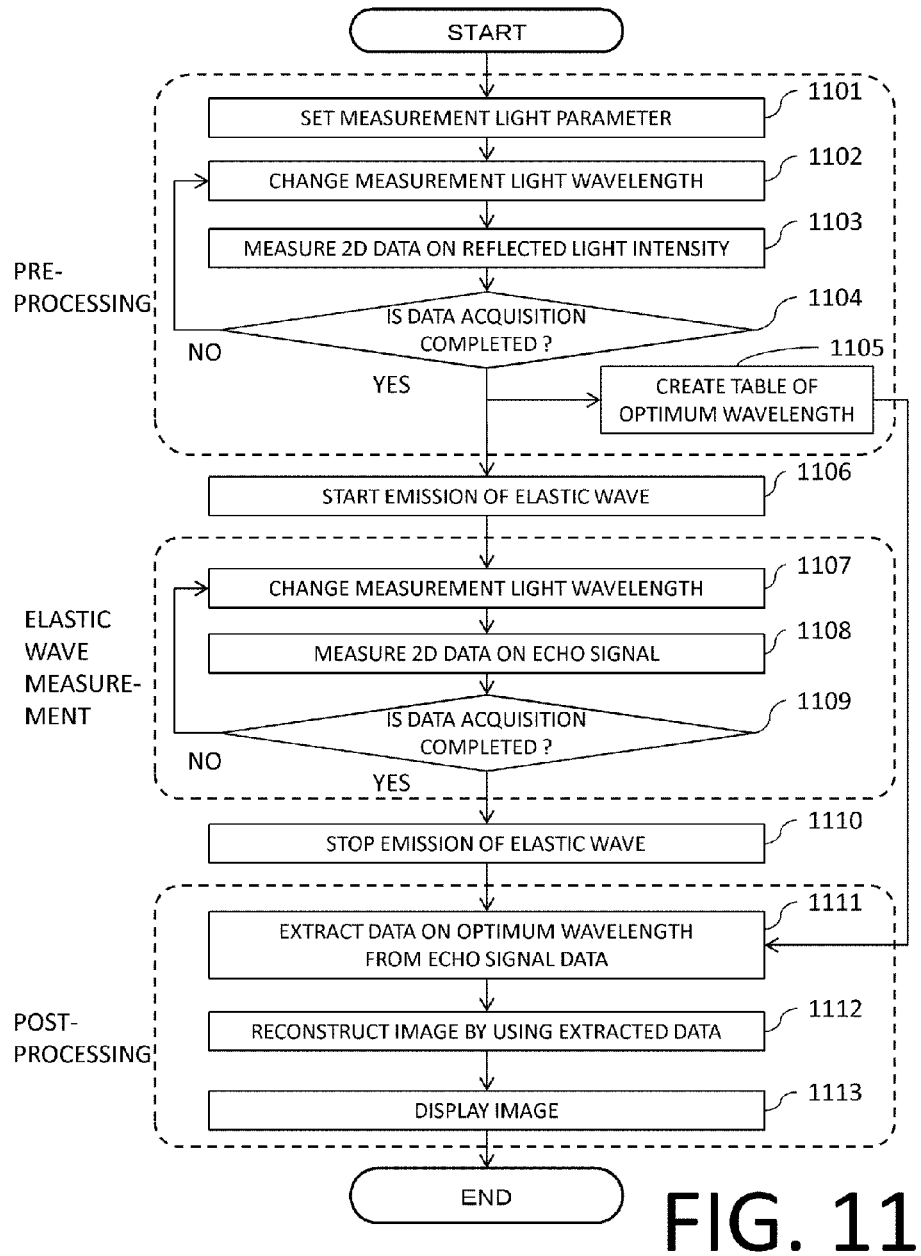
FIG. 11 is a flowchart showing an example of the processing performed by the biological object information imaging apparatus.

Hereinbelow, the flow of the processing and the operation of each constituent element of the apparatus of the present embodiment are described while the flowchart of FIG. 11 is referenced on an as needed basis. In particular, the point different from the flowchart of the first embodiment (FIG. 6) is mainly described.

Steps S1101 to S1105 correspond to pre-processing, and are performed in the same manner as in the first embodiment. First, parameters of the wavelength sweep range and the sweep step of the measurement light 905 are specified (Step S1101). The controller 907 changes and sweeps the wavelength of the measurement light 905 based on the specified wavelength sweep range and sweep step (Step S1102). Since the optimum wavelength varies depending on the degree of variations in the distance between mirrors, the wavelength range to be swept is preferably a wavelength range equal to or exceeding the free spectral range. In addition, the wavelength interval for capturing data when the wavelength dependence of the reflected light amount as shown in FIG. 2 is measured is preferably minimized, and can be set to, e.g., 0.1 nm.

By performing such pre-processing step on every measurement light in the sweep range, the 2D data on the reflected light intensity, i.e., the wavelength dependence of the reflected light amount at each pixel is obtained (Steps S1103 to S1104). Subsequently, by determining the wavelength $\lambda_m$ at which the reflected light amount Ir sharply changes, the table of the optimum wavelength $\lambda_m$ at each pixel is created (Step S1105).

In order to efficiently detect the elastic wave 911 reflected from the object 901 using the Fabry-Perot probe 904, it is desirable to use the acoustic coupling medium between the object 901 and the Fabry-Perot probe 904. FIG. 9 is the drawing in which water is used as the acoustic coupling medium and the object is disposed in a water bath 912, and the acoustic coupling medium may appropriately be interposed between the object 901 and the Fabry-Perot probe 904, and further between the object 901 and the transducer 903. For example, a configuration may also be adopted in which a matching gel is applied to be interposed between the object 901 and the Fabry-Perot probe 904, and further between the object 901 and the transducer 903.

In order to detect the elastic wave 911 using the Fabry-Perot probe 904, it is necessary to measure the change in the reflected light amount of the measurement light at the optimum wavelength $\lambda_m$ or the wavelength in the vicinity thereof. Accordingly, a program that sweeps the wavelength of the measurement light 905 for detecting the elastic wave 911 while sweeping the wavelength of the measurement light 905 is set in the controller 907. The sweep program to be set includes parameters such as the wavelength sweep range, the sweep step, the sweep speed, and the sweep time. As the sweep range and the sweep step of the wavelength of the measurement light 905, values specified when the above-described table of the optimum wavelength is created are used. The controller 907 sweeps the wavelength of the measurement light 905 according to the specified program.

Figure 10:
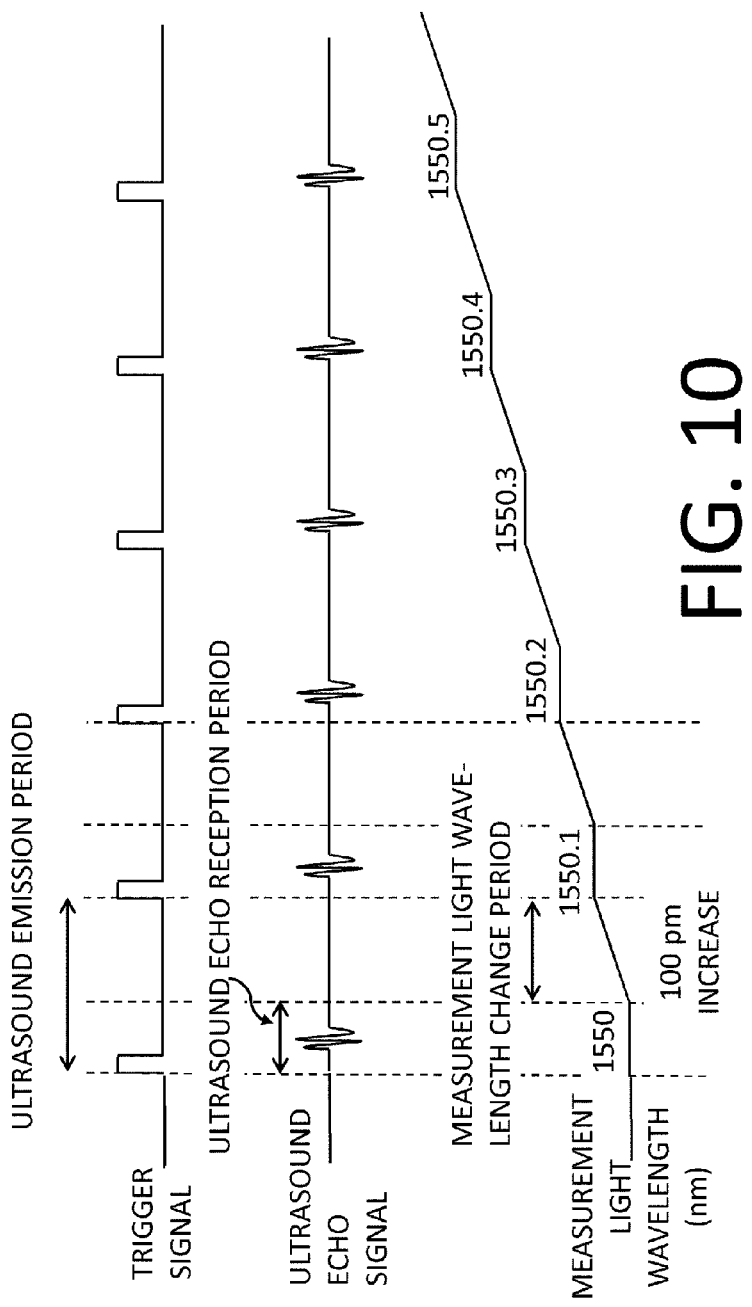
FIG. 10 is a time chart showing an example of processing performed by the biological object information imaging apparatus.

FIG. 10 shows an example of a time chart of the irradiation of the elastic wave 902 (typically ultrasound), the wavelength sweep of the measurement light 905, and the measurement of the elastic wave. First, upon receiving the input signal from the pulser 913, the elastic wave 902 is irradiated to the object 901 by the transducer 903 (Step S1106). Then, by using the electric signal outputted from the pulser 913 as a trigger (uppermost portion of FIG. 10: trigger signal), the elastic wave 911 reflected in the object 901 is measured (second portion of FIG. 10: ultrasound echo signal reception period). Thereafter, before the next elastic wave 902 is emitted, the wavelength of the measurement light 905 is increased by the input value (100 pm in this case). After the wavelength thereof is increased, at the next trigger, the elastic wave 911 is measured. This operation is repeated until the sweep of the specified wavelength range is ended (lowermost portion of FIG. 10). With this, in the sweep range of the wavelength of the measurement light 905, the change in the reflected light amount at each pixel when the elastic wave 911 reaches the Fabry-Perot probe 904 is measured at the intervals of 100 pm.

Thus, the feature of the present embodiment is that, instead of the irradiation of the excitation light, the transmission and the reception of the elastic wave (ultrasound) are performed in the elastic wave measurement step in Steps S1107 to S1109 and the data in the sweep range is thereby obtained. When the elastic wave measurement step is ended, the emission of the elastic wave is stopped (Step S1110).

Note that FIG. 10 is the time chart in a case where the number of times of data acquisition is one. When the number of times of data acquisition or the pulse rate of the elastic wave oscillation by the pulser 913 is different, it is necessary to change the time program of the controller 907 correspondingly.

Subsequently, the step of post-processing is performed in the same manner as in the first embodiment.

After the end of the measurement of the elastic wave 911, the signal processor 909 extracts the electric signal when the elastic wave 911 at the optimum wavelength enters at each pixel based on the table of the premeasured optimum wavelength for each pixel (Step S1111).

In addition, the signal processor 909 calculates the acoustic impedance distribution in the internal portion of the object 901 based on the distribution of the extracted electric signal at the optimum wavelength for each pixel of the array photosensor 908 (Step S1112). As signal processing for obtaining the acoustic impedance distribution from the obtained distribution of the electric signal, phasing addition or the like may be adopted. The acoustic impedance distribution is imaged in a desired format and displayed (Step S1113).

Note that, as the signal processor 909, any processor can be used as long as the processor is capable of storing the distribution of the time-varying change in the electric signal indicative of the intensity of the elastic wave 911 and converting the distribution thereof into the data on the acoustic impedance distribution using operation means.

FIG. 11 shows the measurement flowchart of the present embodiment. Although, in the present embodiment, the creation of the table of the optimum wavelength is performed as the pre-processing before the execution of the photoacoustic measurement, the creation of the table of the optimum wavelength may also be performed after the execution of the transmission of the elastic wave and the measurement of the echo wave. In addition, similarly to the second embodiment, the creation of the table of the optimum wavelength can also be performed simultaneously with the measurement of the elastic wave.

By using the biological object information imaging apparatus described in the third embodiment, it becomes possible to obtain a high-resolution acoustic impedance distribution image within a short time period by using the Fabry-Perot probe.

Example 1

Next, Example of the present invention is described with reference to the drawings.

The present Example includes the configuration described in the first embodiment. In the present Example, a rubber wire having a diameter of 300 μm that absorbs light and is disposed as the object in a substance obtained by setting a 1 percent intralipid aqueous solution with agar-agar is imaged by using the present invention. A phantom is disposed in water.

As the first and second mirrors of the Fabry-Perot probe, a dielectric multilayer film is used. The dielectric multilayer film is designed so as to have a reflectance of 95% or more in 750 to 900 nm. In the substrate of the Fabry-Perot probe, BK 7 is used. A surface opposite to a surface of the substrate on which the dielectric multilayer film is formed is subjected to the AR coating process such that the reflectance thereof is 1% or less in 750 to 900 nm. Parylene C is used in the spacer film between mirrors, and the film thickness thereof is set to 30 μm. In addition, parylene C is used in the protective film of the probe.

As the measurement light wavelength-tunable light source that emits the measurement light for measuring the reflected light amount of the Fabry-Perot probe, an external cavity laser that is wavelength-tunable in 830 to 870 nm is used.

The measurement light emitted from the external cavity laser is magnified by a convex lens, and is caused to enter the Fabry-Perot probe by using a half mirror and a mirror. The beam size of the entering measurement light is set to 1 cm in diameter. The measurement light reflected in the Fabry-Perot probe is caused to enter a high-speed CCD camera using the half mirror and the mirror, and the measurement is thereby performed. The high-speed CCD camera has 100×100 pixels.

The wavelength of the measurement light wavelength-tunable light source is controlled by PC. The wavelength is changed from 840 nm to 860 nm at intervals of 0.1 nm. At this point, the reflected light amount at each wavelength is measured using CCD and the table of the optimum wavelength is created.

Thereafter, the excitation light is irradiated to the object and the measurement of the photoacoustic wave is started. As the excitation light source for the irradiation of the object, a titanium-sapphire laser is used. The pulse rate of the pulsed light to be emitted is set to 10 Hz, the pulse width is set to 10 nsec, and the wavelength is set to 797 nm.

The wavelength of the measurement light wavelength-tunable light source is set to 840 nm and the measurement of the photoacoustic wave is performed. Subsequently, after the measurement light is changed by 0.1 nm in 30 msec, the measurement of the photoacoustic wave is performed. This operation is repeated until the wavelength of the measurement light wavelength-tunable light source becomes 860 nm.

Thereafter, by using the above-described table of the optimum wavelength, the electric signal when the photoacoustic wave at the optimum wavelength enters is extracted at each pixel. Then, by using the signal, the reconstruction of the image is performed by a universal back projection algorithm.

With this, the rubber wire in the 1 percent intralipid agar-agar as a light diffuser is imaged at the resolution of 100 μm.

Example 2

The present Example includes the configuration described in the second embodiment.

The apparatus configuration and the like other than the measurement flowchart are the same as those in Example 1, and hence the description thereof is omitted.

The excitation light is irradiated to the object and the measurement of the photoacoustic wave is started.

The wavelength of the measurement light wavelength-tunable light source is controlled by PC. The wavelength of the measurement light wavelength-tunable light source is set to 840 nm and the measurement of the photoacoustic wave is performed using the CCD camera. Thereafter, in 50 msec, the reflected light amount of the measurement light in the state where the photoacoustic wave does not enter the Fabry-Perot probe is measured. Thereafter, after the measurement light is changed by 0.1 nm in 30 msec, the measurement of the photoacoustic wave is performed. This operation is repeated until the wavelength of the measurement light wavelength-tunable light source becomes 860 nm.

After the end of the measurement, by using the result of measurement of the reflected light amount of the measurement light in the state where the photoacoustic wave does not enter the Fabry-Perot probe, the table of the optimum wavelength is created.

Thereafter, by using the table of the optimum wavelength, the electric signal when the photoacoustic wave at the optimum wavelength enters is extracted at each pixel. Subsequently, by using the signal, the reconstruction of the image is performed by the universal back projection algorithm.

With this, the rubber wire in the 1 percent intralipid agar-agar as the light diffuser is imaged at high resolution.

Example 3

The present Example includes the configuration described in the third embodiment.

The Fabry-Perot probe, the optical system, and the two-dimensional array sensor are the same as those in Example 1, and hence the description thereof is omitted.

In the present Example, a polyethylene wire having a diameter of 300 µm disposed as an object in a substance obtained by setting a 1 percent intralipid aqueous solution with agar-agar is imaged by using the present invention. A phantom is disposed in water.

The elastic wave is irradiated to the object by using a transducer having a center frequency of 20 MHz. As the transducer, a piezoelectric transducer comprised of PZT is used.

Similarly to Example 1, after the table of the optimum wavelength of the measurement light is created, the elastic wave is irradiated to the object and the measurement of the echo wave is started. The elastic wave to be emitted and transmitted is emitted as a pulsed wave by using a pulser. The pulse rate of the elastic wave is set to 10 Hz.

The wavelength of the measurement light wavelength-tunable light source is set to 840 nm and the measurement of the echo wave resulting from the reflection of the elastic wave in the object. Subsequently, after the measurement light is changed by 0.1 nm in 30 msec, the measurement of the echo wave is performed. This operation is repeated until the wavelength of the measurement light wavelength-tunable light source becomes 860 nm.

Thereafter, by using the table of the optimum wavelength, the electric signal when the echo wave at the optimum wavelength enters is extracted at each pixel. Subsequently, by using the signal, the acoustic impedance distribution in the internal portion of the object is imaged by a reconstruction algorithm using phasing addition.

With this, the polyethylene wire in the agar-agar is imaged at high resolution.

The description has been given thus far mainly of the example of the configuration related to the biological object information imaging apparatus having the biological object as the object in the present specification. According to the biological object information imaging apparatus, for the diagnosis of a tumor, a blood vessel disease, or the like and the follow-up of chemotherapy, it becomes possible to image the optical characteristic value distribution in the internal portion of the biological object, and the concentration distribution of the substance constituting the biological tissue that is obtained from the above-mentioned information, and the biological object information imaging apparatus can be used as a medical diagnostic imaging apparatus.

In addition, persons skilled in the art can easily implement the application of the biological object information imaging apparatus to non-destructive inspection that handles a non-biological substance as the object.

From the foregoing, the present invention can be widely used as the inspection apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-157908, filed on Jul. 19, 2011, which is hereby incorporated by reference herein in its entirety.

The invention claimed is:

1. An acoustic signal receiving apparatus comprising:
a wavelength-tunable light source for irradiating measurement light;
a controller for controlling a wavelength of the measurement light;
a Fabry-Perot probe including a first mirror positioned on a side where the measurement light enters, a second mirror positioned on a side where an elastic wave from an object enters, and a spacer film that is positioned between the first and second mirrors and deforms in response to the entrance of the elastic wave;
an array photosensor for detecting a reflected light amount of the measurement light by the Fabry-Perot probe; and
a signal processor for acquiring an intensity of the elastic wave having entered the Fabry-Perot probe based on a change in the reflected light amount resulting from the deformation of the spacer film, wherein
the controller sweeps the wavelength of the measurement light, and
the signal processor determines, based on the reflected light amount at each position of the Fabry-Perot probe that is acquired at each wavelength subjected to the sweep, the wavelength of the measurement light used at the position.

2. The acoustic signal receiving apparatus according to claim 1, further comprising an excitation light source for irradiating excitation light to the object, wherein the elastic wave from the object is a photoacoustic wave generated from the object to which the excitation light has been irradiated.

3. The acoustic signal receiving apparatus according to claim 2, wherein the excitation light source irradiates the excitation light at a specific interval, and
the controller sweeps the wavelength of the measurement light during a period from when the Fabry-Perot probe receives the photoacoustic wave during a specific reception period in which the excitation light is used as a trigger to when the next excitation light is irradiated.

4. The acoustic signal receiving apparatus according to claim 1, further comprising a transducer for transmitting the elastic wave to the object, wherein the elastic wave from the object is an echo wave of the elastic wave transmitted from the transducer.

5. The acoustic signal receiving apparatus according to claim 4, wherein the transducer transmits the elastic wave at a specific interval, and
the controller sweeps the wavelength of the measurement light during a period from when the Fabry-Perot probe receives the echo wave during a specific reception period in which the transmission of the elastic wave is used as a trigger to when the next transmission is performed.

6. The acoustic signal receiving apparatus according to claim 1, wherein the signal processor performs processing of determining the wavelength of the measurement light used at each position of the Fabry-Perot probe before measurement of the object using the wavelength.

7. The acoustic signal receiving apparatus according to claim 1, wherein the signal processor performs processing of determining the wavelength of the measurement light used at each position of the Fabry-Perot probe simultaneously with measurement of the object using the wavelength.

8. An imaging apparatus comprising:
- the acoustic signal receiving apparatus according to claim 1; and
- an image display for displaying an internal portion of the object imaged based on the intensity of the elastic wave acquired by the signal processor.

* * * * *